United States Patent
Mita et al.

(10) Patent No.: US 6,683,200 B2
(45) Date of Patent: *Jan. 27, 2004

(54) N-SUBSTITUTED-N'-SUBSTITUTED UREA DERIVATIVES AND PHARMACEUTICAL COMPOSITIONS CONTAINING THE DERIVATIVES

(75) Inventors: Shiro Mita, Osaka (JP); Masato Horiuchi, Osaka (JP); Masakazu Ban, Osaka (JP); Hiroshi Suhara, Osaka (JP)

(73) Assignee: Santen Pharmaceutical Co., Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/969,971

(22) Filed: Oct. 4, 2001

(65) Prior Publication Data

US 2002/0068763 A1 Jun. 6, 2002

Related U.S. Application Data

(63) Continuation of application No. PCT/JP00/02268, filed on Apr. 7, 2000.

(30) Foreign Application Priority Data

Apr. 7, 1999 (JP) ............................ 11-100481

(51) Int. Cl.$^7$ .................... C07C 323/44; C07C 327/06; C07C 275/24; A61K 31/17; A61K 31/221
(52) U.S. Cl. ........................ 558/254; 560/9; 560/15; 560/16; 560/29; 560/34; 564/47; 564/56; 564/57; 564/59; 562/621; 562/623
(58) Field of Search ..................... 558/254; 560/9, 560/15, 16, 29, 34; 564/47, 56, 57, 59; 562/621, 623

(56) References Cited

U.S. PATENT DOCUMENTS 4,597,902 A    7/1986  Shanklin et al.

6,534,499 B2 * 3/2003  Mital et al. ............ 514/217.12
2001/0041725 A1   11/2001  Mita et al.

FOREIGN PATENT DOCUMENTS

| EP | 0 331 185 | 9/1989 |
| EP | 0 465 369 A1 | 8/1992 |
| EP | 0 849 256 A1 | 6/1998 |
| EP | 0 903 434 | 3/1999 |
| EP | 0 1 072 591 A1 | 1/2001 |

OTHER PUBLICATIONS

Database CAPLUS on STN, Acc. No. 1987:68242, Noack et al., DD 236744 (abstract).*
Database CAPLUS on STN, Acc. No. 1993:179887, Taniguchi et al., JP 04226452 (abstract).*
Yamazaki, M., *TNF-α,*, Clinical Immunology, vol. 27, No. 10, pp. 1270–1274 (1995), Japan.
Eigler, A., et al., *Taming TNF: strategies to restrain this proinflammatory cytokine*, Immunology Today, vol. 18, No. 10, pp. 487–492 (1997).

* cited by examiner

*Primary Examiner*—Brian Davis
(74) *Attorney, Agent, or Firm*—Burns, Doane, Swecker & Mathis, LLP

(57) ABSTRACT

N-Substituted-N'-substituted urea derivatives represented by the following formula, analogs thereof or pharmaceutically acceptable salts thereof are herein provided. These compounds show a TNF-α production inhibitory activity.

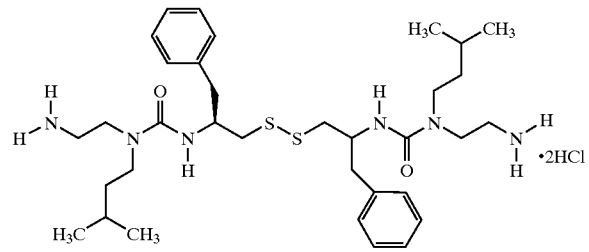

20 Claims, No Drawings

N-SUBSTITUTED-N'-SUBSTITUTED UREA DERIVATIVES AND PHARMACEUTICAL COMPOSITIONS CONTAINING THE DERIVATIVES

This application is a continuation of International Application No. PCT/JP00/02268 filed on Apr. 7, 2000, which International Application was published by the International Bureau in Japanese on Oct. 19, 2000.

BACKGROUND OF THE INVENTION

The present invention relates to a novel N-substituted-N'-substituted urea derivative as well as a pharmaceutical composition, a TNF-α production inhibitory agent and a therapeutic agent for treating an autoimmune disease, which contain the compounds.

TNF-α (Tumor Necrosis Factor-α) has presently been recognized as a cytokine strongly correlated with biological protection-immunological mechanism, but the continuous and excess production of TNF-α causes various tissue disorders and this accordingly becomes a principal cause of a variety of diseases and exacerbation. For instance, examples of pathogenesis associated with TNF-α include articular rheumatism, systemic erythematodes (SLE), dyscrasia, acute infectious diseases, allergy, fever, anemia and diabetes (YAMAZAKI, Clinical Immunology, 1995, 27:1270). Moreover, it has also been reported that TNF-α plays an important role in the crisis of chronic rheumatism and Crohn's disease, which are autoimmune diseases (Andreas Eigler et al., Immunology Today, 1997, 18:487).

Accordingly, a compound capable of inhibiting the production of TNF-α or controlling the action thereof would be effective in the treatment of the foregoing diseases and therefore, a variety of investigations have been done to obtain such a compound (the foregoing articles: YAMAZAKI, Clinical Immunology, 27; Andreas Eigler et al., Immunology Today, 18).

On the other hand, the compounds represented by the following general formula I, in which $R^1$, $R^3$ and $R^4$ simultaneously represent hydrogen atoms and $R^6$ and $R^7$ are both methyl groups, are disclosed in Japanese Un-Examined Patent Publication No. Hei 1-224758 as sensitizing dyes (II-40). In addition, the compounds represented by the following general formula I, in which $R^1$ is an aryl group or a furanylmethyl group, $R^3$ is an isopropyl group and $R^6$ and $R^7$ are both methyl groups, are disclosed in Japanese Un-Examined Patent Publication No. Sho 57-209267 as examples of the compounds having an effect as an antiarrhythmic agent (Examples 1, 2, 34, 37, 52 and 58).

DISCLOSURE OF THE INVENTION

An object of the present invention is to provide a novel compound having an activity of inhibiting TNF-α production.

It is another object of the present invention to provide an intermediate useful in the preparation of the foregoing compound.

It is a further object of the present invention to provide a pharmaceutical composition, a TNF-α production inhibitory agent and a therapeutic agent for treating autoimmune diseases, which comprise the foregoing compounds.

The inventors of this invention have conducted intensive studies to synthesize a compound having a urea structure as a basic structure, which has not conventionally been investigated as a drug, have established a large number of novel compounds, have found that N-substituted-N'-substituted urea derivatives represented by the following general formula I among the foregoing novel compounds show an excellent TNF-α production inhibitory activity and thus have completed the present invention on the basis of the foregoing finding.

More specifically, the present invention herein provides an N-substituted-N'-substituted urea derivative represented by the following general formula I and a pharmaceutically acceptable salt thereof:

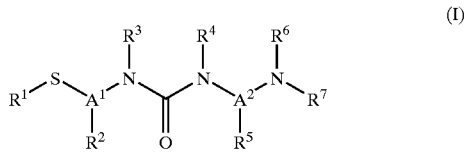

wherein $R^1$ represents a hydrogen atom, a lower alkyl group, an aryl group or a group represented by the following general formula II:

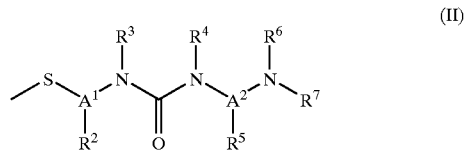

wherein $R^2$ represents a hydrogen atom, a lower alkyl group, a cycloalkyl group, an aryl group, a carboxyl group or an ester group, or $R^2$ may form a ring together with $R^1$; $R^3$ and $R^4$ may be the same or different and each represents a hydrogen atom, a lower alkyl group, a cycloalkylalkyl group, an arylalkyl group, a cycloalkyl group or an aryl group; $R^5$ represents a hydrogen atom, a lower alkyl group, a hydroxyl group, a lower alkoxy group or an aryl group; $R^6$ and $R^7$ may be the same or different and each represents a hydrogen atom, a lower alkyl group, a cycloalkylalkyl group, a cycloalkyl group or an aryl group; $A^1$ and $A^2$ may be the same or different and each represents a lower alkylene group, provided that if both $R^6$ and $R^7$ are methyl groups, $R^1$, $R^3$ and $R^4$ do not simultaneously represent hydrogen atom, or if $R^3$ is an isopropyl group and both $R^6$ and $R^7$ are methyl groups, $R^1$ does not represent an aryl group and a furanylmethyl group.

According to the present invention, there are also provided N-substituted-N'-substituted urea derivatives represented by the following general formula III and salts thereof:

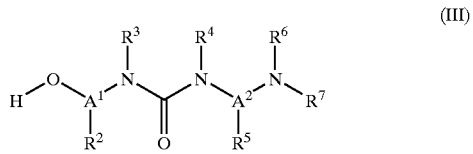

The present invention likewise provides a pharmaceutical composition, a TNF-α production inhibitory agent and a therapeutic agent for treating autoimmune diseases, which comprise the foregoing N-substituted-N'-substituted urea derivative or a pharmaceutically acceptable salt thereof.

BEST MODE FOR CARRYING OUT THE INVENTION

In the present invention, the lower alkyl group may be, for instance, linear or branched alkyl groups having 1 to 8 carbon atoms such as methyl, ethyl, propyl, isopropyl, butyl, isobutyl, t-butyl, pentyl, isopentyl and isohexyl groups, with alkyl groups having 1 to 6 being preferred. The lower alkyl group is more preferably those having 1 to 3 carbon atoms, in particular, methyl group. Examples of cycloalkyl groups are those having 3 to 10 carbon atoms such as cyclopropyl, cyclobutyl, cyclopentyl, cyclohexyl and cycloheptyl groups, with those having 3 to 6 carbon atoms being preferred and cyclohexyl group being particularly preferred. Examples of lower alkoxy groups include linear or branched alkoxy groups having 1 to 8 carbon atoms such as methoxy, ethoxy, propoxy, isopropoxy, butoxy and hexyloxy groups, with those having 1 to 5 carbon atoms being preferred and those having 1 to 3 carbon atoms being particularly preferred.

These lower alkyl, cycloalkyl and lower alkoxy groups may be substituted with for instance, halogen atoms (such as fluorine, chlorine, iodine and bromine atoms) and/or a hydroxyl group. Moreover, the cycloalkyl group may be substituted with a lower alkyl group and/or a lower alkoxy group.

Examples of lower alkylene groups are linear or branched alkylene groups having 1 to 8 carbon atoms such as methylene, ethylene, propylene, isopropylene, methylmethylene, tetramethylene, 2-methyltlimethylene and hexamethylene groups, with those having 1 to 5 carbon atoms being preferred. The lower alkylene group is more preferably those having 2 to 4 carbon atoms and in particular, those having 2 to 3 carbon atoms.

In addition, examples of aryl groups are phenyl groups, naphthyl groups and aromatic heterocyclic groups having 6 to 12 carbon atoms, which may be substituted or unsubstituted and the aryl group is preferably a substituted or unsubstituted phenyl group and particularly preferably an unsubstituted phenyl group or a biphenylyl group. In this respect, the substituent may be, for instance, a halogen atom (such as fluorine, chlorine, iodine or bromine atom), a hydroxyl group, an amino group, a lower alkyl group, a lower alkoxy group, a cycloalkyl group or a phenyl group.

Examples of cycloalkylalkyl and arylalkyl groups are linear or branched alkyl groups having 1 to 8 carbon atoms, preferably alkyl groups having 1 to 5 carbon atoms, more preferably alkyl groups having 1 to 3 carbon atoms and most preferably ethyl group, to which the foregoing cycloalkyl or aryl group is bonded.

Examples of ester groups are lower alkyl esters, benzyl esters and phenyl esters.

Examples of rings formed by the combination of substituents $R^2$ and $R^1$ are 5- and 6-membered non-aromatic hetero rings including the sulfur atom to which $R^1$ is bonded as a member of the rings, such as tetrahydrothiophene, thiolactone and dithiolan.

When the compound represented by the general formula I according to the present invention has thiol, hydroxyl and/or amino groups, these groups may be protected with commonly used protective groups.

Examples of protective groups for thiol group are those commonly used as protective groups for thiol group such as acyl groups and substituted thio groups. Specific examples thereof are acyl groups such as lower alkanoyl groups, phenylcarbonyl groups, thenoyl groups, nicotinoyl groups, lower alkoxycarbonyl groups, substituted lower alkoxycarbonyl groups and substituted carbamoyl groups; and substituted thio groups such as lower alkylthio groups and phenylthio group. In this connection, the phenyl lings of the foregoing phenylcarbonyl and phenylthio groups may be substituted with a halogen atom, a lower alkyl group, a lower alkoxy group or a nitro group.

Among these, preferred are, for instance, acyl groups such as acetyl group, propionyl group, butyryl group, pivaloyl group, benzoyl group, thenoyl group, t-butoxycarbonyl group and benzyloxycarbonyl group; and substituted thio groups such as ethylthio, t-butylthio and phenylthio groups, with lower alkylcarbonyl groups (in particular, those having 2 to 5 carbon atoms) being more preferably used.

Protective groups for hydroxyl group may be, for instance, those commonly used as the protective groups for hydroxyl group such as acyl groups, substituted lower alkyl groups and substituted silyl groups. Specific examples thereof are acyl groups such as formyl group, lower alkanoyl groups, halogenated lower alkanoyl groups, phenylcarbonyl groups, lower alkoxycarbonyl groups and phenyl lower alkoxycarbonyl groups; substituted lower alkyl groups such as allyl group, lower alkoxy lower alkyl groups, substituted lower alkoxy lower alkyl groups, phenyl lower alkyl groups, tetrahydropyranyl groups and tetrahydrofuranyl groups; and substituted silyl groups such as lower alkyl silyl groups and phenyl silyl group. In this respect, the phenyl rings of the foregoing phenylcarbonyl, phenyl lower alkoxycarbonyl, phenyl lower alkyl and phenyl silyl groups may be substituted with a halogen atom, a lower alkyl group, a lower alkoxy group or a nitro group.

Among these protective groups, preferred are acyl groups such as formyl, acetyl, pivaloyl, monochloroacetyl, trichloroacetyl, trifluoroacetyl, benzoyl, methoxycarbonyl, ethoxycarbonyl, isobutoxycarbonyl, t-butoxycarbonyl and benzyloxycarbonyl groups, substituted alkyl groups such as allyl, methoxymethyl, 1-ethoxyethyl, 2-methoxyethoxymethyl, benzyloxymethyl, benzyl, 4-methoxybenzyl, trityl, 2-tetrahydropyranyl and 2-tetrahydrofuranyl groups, and substituted silyl groups such as trimethyl silyl, triethyl silyl, triisopropyl silyl, t-butyldimethyl silyl and t-butyldiphenyl silyl groups, with tri(lower alkyl) silyl groups being more preferred.

Examples of protective groups for amino group are those commonly used as protective groups for amino group such as acyl groups, substituted lower alkyl groups and substituted sulfonyl groups. Specific examples thereof are acyl groups such as formyl, lower alkanoyl, halogenated lower alkanoyl, phenylcarbonyl, lower alkoxycarbonyl, substituted lower alkoxycarbonyl and phenoxycarbonyl groups; substituted lower alkyl groups such as allyl, phenyl lower alkyl and benzoyl lower alkyl groups; and substituted sulfonyl groups such as lower alkyl sulfonyl and phenyl sulfonyl groups. In this connection, the phenyl rings of the foregoing phenylcarbonyl, phenoxycarbonyl, phenyl lower alkyl, benzoyl lower alkyl and phenyl sulfonyl groups may be substituted with a halogen atom, a lower alkyl group, a lower alkoxy group or a nitro group.

Among these protective groups, preferred are acyl groups such as formyl, acetyl, trichloroacetyl, trifluoroacetyl, benzoyl, methoxycarbonyl, isobutoxycarbonyl, t-butoxycarbonyl, allyloxycarbonyl, 2,2,2-trichloroethoxycarbonyl, benzyloxycarbonyl, diphenylmethoxycarbonyl and phenoxycarbonyl groups; substituted alkyl groups such as allyl, benzyl, trityl and (4-methoxyphenyl) diphenylmethyl groups; and substituted sulfonyl groups such as benzenesulfonyl, 2,4,6-trimethylbenzenesulfonyl and toluenesulfonyl groups, with lower alkoxycarbonyl groups being more preferred.

In the compound of Formula I according to the present invention, $R^1$ is preferably a hydrogen atom, a lower alkyl group or a group represented by Formula II and if $R^1$ represents a hydrogen atom, preferred compounds include those protected with thiol protective groups at the position of the substituent $R^1$. Moreover, $R^1$ is preferably a hydrogen atom or a group represented by Formula II and if $R^1$ represents a hydrogen atom, preferred compounds include those necessarily protected with thiol protective groups at the position of the substituent $R^1$. In addition, if $R^1$ is a lower alkyl group, the lower alkyl group is preferably an unsubstituted one.

The substituent $R^2$ is preferably a hydrogen atom or an aryl group. If $R^2$ is an aryl group, the aryl group is preferably bonded to the $2^{nd}$ or $3^{rd}$ carbon atom of the substituent $A^1$, while the carbon atom of $A^1$ bonded to the S atom is defined to be the $1^{st}$ carbon atom, with the aryl group bonded to the $2^{nd}$ carbon atom of the substituent $A^1$ being more preferred.

$R^3$ and $R^4$ may be the same or different and each preferably represents a hydrogen atom, a lower alkyl group, a cycloalkylalkyl group or an arylalkyl group. Moreover, $R^3$ is preferably a cycloalkylalkyl group or an arylalkyl group and $R^4$ is preferably a hydrogen atom, a lower alkyl group or an arylalkyl group.

In particular, the foregoing substituents $R^3$ and $R^4$ are different from one another. Among these, one of them preferably represents a hydrogen atom. The lower alkyl groups represented by the substituents $R^3$ and $R^4$ are preferably linear or branched alkyl groups having 4 to 8 carbon atoms and, in particular, alkyl groups having 4 to 6 carbon atoms, with an isopentyl group being more preferred.

The substituent $R^5$ preferably represents a hydrogen atom, a lower alkyl group, a hydroxyl group or an aryl group, with a hydrogen atom, a lower alkyl group and an aryl group being more preferred. If $R^5$ represents a hydroxyl group, it may be protected with a hydroxyl group-protecting group. If $R^5$ represents a group other than a hydrogen atom, $R^5$ is preferably bonded to the $1^{st}$, $2^{nd}$ or $3^{rd}$ carbon atom of the substituent $A^2$, while the carbon atom of the substituent $A^2$ bonded to the nitrogen atom constituting a urea is defined to be the $1^{st}$ carbon atom. More preferably, $R^5$ is bonded to the $1^{st}$ or $_2$nd carbon atom of the substituent $A^2$.

$R^6$ and $R^7$ may be the same or different and each preferably represents a hydrogen atom, a lower alkyl group or an aryl group. More preferably, $R^6$ represents a hydrogen atom or a lower alkyl group and $R^7$ represents a hydrogen atom, a lower alkyl group or an aryl group. In addition, if $R^6$ and/or $R^7$ are hydrogen atoms, they may be protected with amino group-protecting groups.

$A^1$ and $A^2$ may be the same or different and each preferably represents a lower alkylene group having 2 to 4 carbon atoms and, in particular, $A^1$ is preferably a lower alkylene group having 2 or 3 carbon atoms.

Moreover, if $R^6$ and $R^7$ in the general formula I are both alkyl groups, it is preferred that $R^1$, $R^3$ and $R^4$ do not simultaneously represent hydrogen atoms. In addition, $R^3$, $R^6$ and $R^7$ simultaneously represent alkyl groups, it is preferred that $R^1$ does not represent an aryl group or a substituted lower alkyl group.

Among the compounds of the present invention represented by Formula I, preferred are those listed below:

(i) Compounds of Formula I wherein $R^1$ is a hydrogen atom, a lower alkyl group or a group represented by Formula II, $R^2$ is a hydrogen atom or an aryl group, $R^3$ and $R^4$ may be the same or different and each represents a hydrogen atom, a lower alkyl group, a cycloalkylalkyl group or an arylalkyl group, $R^5$ is a hydrogen atom, a lower alkyl group, a hydroxyl group or an aryl group, $R^6$ and $R^7$ may be the same or different and each represents a hydrogen atom, a lower alkyl group or an aryl group, and $A^1$ and $A^2$ may be the same or different and each represents an alkylene group having 2 to 4 carbon atoms.

(ii) Compounds of Formula I or those specified in the foregoing item (i) wherein $R^6$ represents a hydrogen atom or a lower alkyl group, $R^7$ represents a hydrogen atom, a lower alkyl group or an aryl group, $A^1$ is an alkylene group having 2 or 3 carbon atoms and $A^2$ is an alkylene group having 2 to 4 carbon atoms.

(iii) Compounds of Formula I or those specified in the foregoing item (i) or (ii) wherein $R^3$ is a hydrogen atom, a cycloalkylalkyl group or an arylalkyl group, $R^4$ is a hydrogen atom, a lower alkyl group or an arylalkyl group and either of $R^3$ or $R^4$ represents a hydrogen atom.

(iv) Compounds of Formula I or those specified in the foregoing item (i) to (iii) wherein $R^5$ is a hydrogen atom, a lower alkyl group or an aryl group.

(v) In the foregoing definition (i) to (iv), the thiol group is protected with a lower alkylcarbonyl group, the hydroxyl group is protected with a tri (lower alkyl) silyl group and the amino group is protected with a lower alkoxycarbonyl group.

Specific examples of preferred compounds of the present invention are at least one member selected from the group consisting of 1-[2-(acetylthio) ethyl]-3-[(1S)-1-benzyl-2-(dimethylamino)ethyl]-1-phenethyl urea, 1-[(1S)-2-(acetylthio)-1-benzylethyl]-3-[2-(dimethylamino) ethyl]-3-isopentyl urea, 1-[(1S)-2-(acetylthio)-1-[(4-biphenylyl) methyl]ethyl]-3-[2-(dimethylamino)ethyl]-3-isopentyl urea, bis[(2S)-2-[3-(2-aminoethyl)-3-isopentyl ureido]-3-phenylpropane] disulfide and bis[(2S)-2-[3-(2-aminoethyl)-3-isopentyl ureido]-3-(4-biphenylyl) propane] disulfide as well as pharmaceutically acceptable salts thereof.

The salts used in the present invention are not restricted to any particular one inasmuch as they are pharmaceutically acceptable salts and examples thereof are salts with inorganic acids such as hydrochloric acid, nitric acid and sulfuric acid, salts with organic acids such as acetic acid, fumaric acid, maleic acid, tartaric acid and citric acid. And salts with alkali metals or alkaline earth metals such as sodium, potassium and calcium. In addition, the compound of the present invention may form a geometrical isomer or an optical isomer, these isomers likewise fall within the scope of the present invention. Moreover, the compound of the present invention may be in the form of a hydrate.

The compounds of the present invention represented by the general formula I may be synthesized by, for instance, the following representative method or those similar to the same.

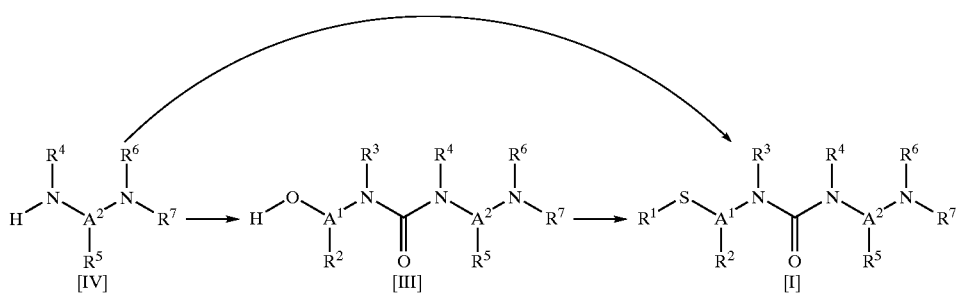

The foregoing method includes the following two synthetic methods A and B.

Synthetic Method A: Compounds of Formula [IV] →Compounds of Formula [III]→Compounds of Formula I Synthetic Method B: Compounds of Formula [IV] →Compounds of Formula I These synthetic methods will be detailed below.

Synthetic Method A:

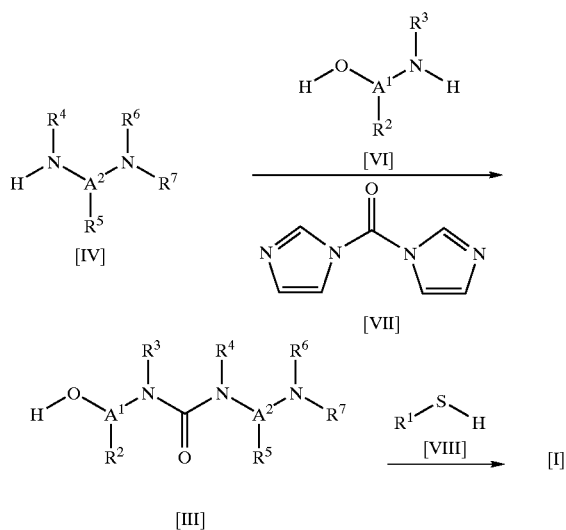

A compound of Formula [IV] is reacted with an aminoalcohol derivative [VI] in the presence of a condensation agent (such as 1,1'-carbonyl diimidazole [VII]) to give a compound of Formula [III] and then the resulting compound of Formula [III] and a thio derivative [VIII] are condensed together according to the Mitsunobu reaction to give a compound represented by the general formula I according to the present invention.

Synthetic Method B:

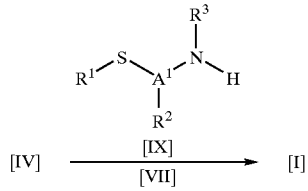

A compound of Formula [IV] is reacted with a compound of Formula [IX] in the presence of a condensation agent (such as 1,1'-carbonyl diimidazole [VII]) to directly give a compound represented by the general formula I according to the present invention. In this respect, the compound of Formula [IV] and the compound of Formula [IX] can easily be synthesized according to the method disclosed in Japanese Patent Application Serial No. Hei 10-79154.

The compounds of the foregoing Formula [III] are novel compounds and useful intermediates for use in the preparation of the compounds represented by the general formula I according to the present invention. In the foregoing formula, $R^2$, $R^3$, $R^4$, $R^5$, $R^6$, $R^7$, $A^1$ and $A^2$ are the same as those defined above in connection with the general formula I and preferred examples thereof are likewise the same as those described above in connection with the general formula I.

In the foregoing synthetic methods, if a reactant includes a thiol, hydroxyl or amino group, in the molecule, these groups may, if necessary, be protected with appropriate protective groups and these protective groups may be removed after the completion of the reaction according to the usual methods. In addition, if a reactant includes a carboxyl group in the molecule, the carboxyl group may, if necessary, be esterified and the ester may be converted into a carboxylic acid through hydrolysis.

In the compound of the present invention, if $R^2$ is linked with the sulfur atom adjacent to $A^1$ to form a thiolactone ring, the compound of the present invention can likewise be prepared according to the following method in addition to the aforementioned route. More specifically, if $R^2$ represents a carboxyl group and $R^1$ represents a hydrogen atom in Formula [I], the thiolactone ring may be synthesized by condensing these groups.

The compounds prepared according to the foregoing method may be converted into the corresponding salts detailed above according to the usual methods.

The TNF-α production inhibitory action of the compounds according to the present invention will be described in the following section entitled "Pharmacological Tests". In the tests, the inhibitory effects of the compounds on the release of TNF-α induced by the stimulation of lipopolysaccharide (LPS) were investigated in vitro. As a result, it was found that the compounds of the present invention clearly showed an excellent TNF-α production inhibitory action.

It has been known that the productivity of TNF-α is closely related to the crisis of, for instance, autoimmune diseases such as articular rheumatism, Crohn's disease and systemic erythematodes, dyscrasia, acute infectious diseases, allergy, fever, anemia and diabetes. Accordingly, compounds having an effect of inhibiting the production thereof such as those of the present invention would be expected to be useful as drugs for treating wide variety of these diseases.

The compound of the present invention may be administered through oral and parenteral routes. Examples of the dosage forms of the compounds include tablets, capsules, granules, powders and injections and they can be formed into these pharmaceutical preparations using techniques currently used in the art. For instance, oral drugs such as tablets, capsules, granules and powders may be prepared by, if necessary, incorporating, into the compound, a thickening agent such as lactose, crystalline cellulose, starch and vegetable oils, a lubricant such as magnesium stearate and talc, a binder such as hydroxypropyl cellulose and polyvinyl pyrolidone, a disintegrator such as carboxymethyl cellulose, calcium and low substituted hydroxypropylmethyl cellulose, a coating agent such as hydroxypropylmethyl cellulose, macrogol and silicone resin, and a film-forming agent such as gelatin film.

The dose of the compound of the present invention may appropriately be selected depending on, for instance, the symptoms and age of each particular patient and the dosage forms, but it usually ranges from 0.1 to 5000 mg, preferably 1 to 1000 mg per day for the oral administration, which may be administered at a time or over several times in portions.

Preparation Examples of the compounds of the present invention, Examples of pharmaceutical preparations and the results of Pharmacological Tests will be given below, but they are given for deepening the understanding of the present invention and never limit the scope of the present invention at all.

PREPARATION EXAMPLES

Reference Example 1:

(1S)-1-Benzyl-2-(dimethylamino) Ethylamine (Reference Compound 1-1)

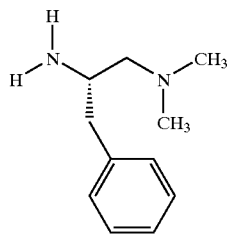

Lithium aluminum hydride (759 mg) was suspended in anhydrous ether (20 ml) with ice cooling in the nitrogen gas atmosphere and then a solution of (2S)-2-amino-$N^1,N^1$-dimethyl-3-phenylpropionamide (1.92 g) in anhydrous tetrahydrofuran (10 ml) was dropwise added to the resulting suspension. This mixture was stirred at room temperature for 1.5 hour. Ethyl acetate was gradually and dropwise added to the reaction liquid till the latter did not undergo foaming any more, with ice cooling. Then a 2N aqueous sodium hydroxide solution was added to the reaction liquid and the resulting mixture was extracted with chloroform. The organic phase thus obtained was dried over anhydrous sodium sulfate and then concentrated under reduced pressure. The resulting oily product was purified through the silica gel column chromatography to give the title compound (Reference Compound 1-1, 1.35 g).

(Reference Compound 1-1)

[α] D20:+15.3° (c=1.0, chloroform)

IR (Film, cm$^{-1}$): 3289, 2940, 2769, 1601, 1495, 1357 and 1264

The procedures similar to those used in Reference Example 1 were repeated to give the following compound.

(1S)-1-Benzyl-2-(dimethylamino)-N-phenethyl ethylamine dihydrochloride (Reference Compound 1-2)

[α] D20:+4.0° (c=1.0, methanol)

IR (Film, cm$^{-1}$): 3407, 2950, 2691, 1456, 750 and 701

Reference Example 2:

N-Phenethyl-2-(dimethylamino) Ethylamine Dihydrochloride (Reference Compound 2-1)

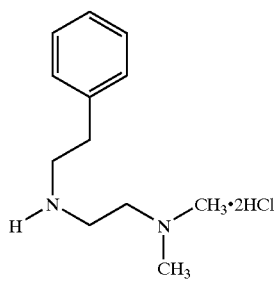

To a solution of phenethyl bromide (3.00 g) in ethanol (54 ml), there were added 2-(dimethylamino) ethylamine (2.14 g) and sodium iodide (7.29 g) and the resulting mixture was refluxed with heating overnight with stirring. The reaction liquid was concentrated under reduced pressure, followed by the addition of water to the resulting residue and the extraction of the reaction liquid with chloroform. The resulting organic phase was washed with saturated sodium chloride aqueous solution, dried over anhydrous magnesium sulfate and concentrated under reduced pressure. The resulting oily product was dissolved in chloroform (5 ml) and a 4.6N solution of hydrogen chloride in ethyl acetate (8 ml) was added to the chloroform solution with ice cooling. The resulting precipitates were filtered off to thus give the title compound (Reference Compound 2-1, 2.23 g) in the form of crystals.

(Reference Compound 2-1)

mp: 180° C.

IR (KBr, cm$^{-1}$): 3400, 2957, 2710, 2442, 1471, 762 and 702

The procedures similar to those used in Reference Example 2 were repeated to give the following compounds.

N-Isopentyl-2-(dimethylamino) ethylamine (Reference Compound 2-2)

IR (Film, cm–1): 3307, 2954, 2818, 1464 and 753

2-(t-Butoxycarboxamido)-N-isopentyl ethylamine (Reference Compound 2-3)

IR (Film, cm$^{-1}$): 3339, 2957, 1701, 1522, 1367, 1274, 1251, 1174 and 755

Example 1:

1-(2-Cyclohexylethyl)-3-[2-(dimethylamino)ethyl]-1-(2-hydroxyethyl) Urea (Compound 1-1)

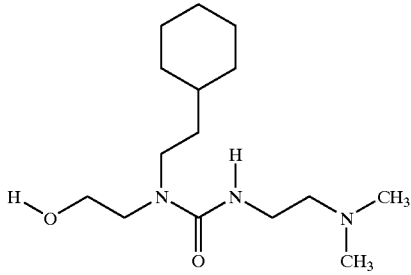

1,1'-Carbonyldiimidazole (0.43 g) was dissolved in a solution of 2-(dimethylamino) ethylamine (0.19 g) in anhydrous tetrahydrofuran (11 ml) in the nitrogen gas atmosphere and the resulting solution was stirred at room temperature for 20 minutes. To the reaction solution, there was added N-(2-hydroxyethyl)-2-cyclohexyl ethylamine hydrochloride (0.50 g) and the mixture was refluxed with heating for 3 hours. Chloroform was added to the reaction solution with ice cooling, followed by washing the mixture with saturated sodium hydrogen carbonate aqueous solution and then with saturated sodium chloride aqueous solution, drying over anhydrous magnesium sulfate and concentrating under reduced pressure. The resulting oily product was purified through the silica gel column chromatography to thus give the title compound (Compound 1-1, 0.68 g).

(Compound 1-1)

IR (Film, $cm^{-1}$): 3354, 2922, 2851, 1628, 1538, 1448, 1405, 1374, 1268 and 1054

The procedures similar to those used in Example 1 were repeated to thus give the following compounds.

1-(2-Cyclohexylethyl)-3-[3-(dimethylamino) propyl]-1-(2-hydroxyethyl) urea (Compound 1-2)

IR (Film, $cm^{-1}$): 3339, 2923, 2851, 1626, 1536, 1448, 1406, 1372, 1266, 1171 and 1053

1-[(1S)-1-Benzyl-2-(dimethylamino) ethyl]-3-(2-hydroxyethyl)-3-phenethyl urea (Compound 1-3)

IR (Film, $cm^{-1}$): 3117, 2939, 1623, 1534, 1496, 1454, 1407, 1326, 1257 and 1063

1-(2-Cyclohexylethyl)-1-(2-hydroxyethyl)-3-[3-[(N-methyl)phenylamino] propyl] urea (Compound 1-4)

IR (Film, $cm^{-1}$): 3323, 2922, 2850, 1621, 1600, 1541, 1507, 1448, 1407, 1372, 1270, 1229, 1197, 1132, 1054 and 748

1-[2-(Dimethylamino)ethyl]-3-(2-hydroxyethyl)-3-isopentyl urea (Compound 1-5)

IR (Film, $cm^{-1}$): 3353, 2954, 1632, 1537, 1467, 1406, 1367, 1236, 1056 and 756

1-(2-Cyclohexylethyl)-1-(2-hydroxyethyl)-3-[2,2-dimethyl-3-(dimethylamino) propyl] urea (Compound 1-6)

IR (Film, $cm^{-1}$): 3178, 2923, 2852, 2777, 1624, 1533, 1451, 1257, 1064, 843 and 745

Example 2:

1-[(1S)-1-Benzyl-2-(benzyloxy)ethyl]-3-[2-(dimethylamino)ethyl]-3-phenethyl Urea (Compound 2-1)

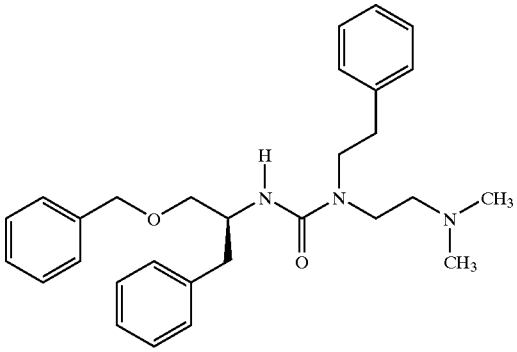

To a solution of (1S)-1-benzyl-2-(benzyloxy) ethylamine hydrochloride (351 mg) in anhydrous tetrahydrofuran (4.2 ml), there were added imidazole (87 mg) and 1,1'-carbonyl diimidazole (268 mg) in the nitrogen gas atmosphere and the resulting mixture was stirred at room temperature for 15 minutes. To the reaction liquid, there was added N-phenethyl-2-(dimethylamino) ethylamine di-hydrochloride (Reference Compound 2-1, 408 mg), followed by the reflux of the resulting mixture under heating for one hour. Water was added to the reaction liquid with ice cooling and the mixture was extracted with ethyl acetate. The resulting organic phase was washed with saturated sodium chloride aqueous solution, dried over anhydrous magnesium sulfate and then concentrated under reduced pressure. The resulting oily product was purified through the silica gel column chromatography to give the title compound (Compound 2-1, 532 mg).

(Compound 2-1)

[α] D20:−10.7° (c=1.0, chloroform)

IR (Film, $cm^{-1}$): 2944, 1647, 1496, 1453, 1253, 1027, 746 and 699

The procedures similar to those used in Example 2 were repeated to give the following compounds.

1-[(1S)-1-Benzyl-2-(benzyloxy)ethyl]-3-[2-(dimethylamino)ethyl]-3-isopentyl urea (Compound 2-2)

[α] D20:−8.5° (c=0.57, chloroform)

IR (Film, $cm^{-1}$): 3357, 3222, 2952, 1647, 1496, 1454, 1252, 747 and 700

1-[(1S)-1-Benzyl-2-(benzyloxy)ethyl]-3-[(1S)-1-benzyl-2-(dimethylamino)ethyl]-3-phenethyl urea (Compound 2-3)

[α] D20:−40.1° (c=0.57, chloroform)

IR (Film, $cm^{-1}$): 3458, 3026, 2937, 2858, 1646, 1496, 1454, 746 and 700

1-[(1S)-1-Benzyl-2-(benzyloxy) ethyl]-3-[2-(t-butoxycarboxamido) ethyl]-3-isopentyl urea (Compound 2-4)

[α] D20:−17.40 (c=0.66, chloroform)

IR (Film, $cm^{-1}$): 3324, 2956, 2868, 1688, 1631, 1516, 1366, 1283, 1251, 1171, 764 and 699

Example 3:

1-[(1S)-1-Benzyl-2-hydroxyethyl]-3-[2-(dimethylamino)ethyl]-3-phenethyl urea (Compound 3-1)

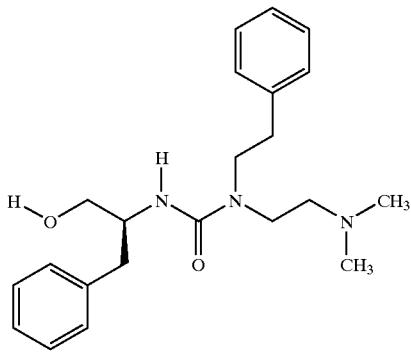

To a solution of 1-[(1S)-1-benzyl-2-(benzyloxy)ethyl]-3-[2-(dimethylamino)ethyl]-3-phenethyl urea (Compound 2-1, 414 mg) in ethanol (4.5 ml), there was added 20% palladium hydroxide-on-carbon (100 mg) in the nitrogen gas atmosphere. This mixture was stirred for 3 days in the hydrogen gas atmosphere. The palladium-on-carbon was removed by the filtration through celite and the resulting filtrate was concentrated under reduced pressure to thus give the title compound (Compound 3-1, 299 mg).

(Compound 3-1)

[α] D20:−54.6° (c=1.0, dimethyl sulfoxide)

IR (Film, cm$^{-1}$): 3346, 2949, 1622, 1538, 750 and 702

The procedures similar to those used in Example 3 were repeated to give the following compounds.

1-[(1S)-1-Benzyl-2-hydroxyethyl]-3-[2-(dimethylamino) ethyl]-3-isopentyl urea (Compound 3-2)

[α] D20:−47.6° (c=0.50, dimethyl sulfoxide)

IR (Film, cm$^{-1}$): 3423, 2957, 1626 and 1538

1-[(1S)-1-Benzyl-2-(dimethylamino)ethyl]-3-[(1S)-1-benzyl-2-hydroxyethyl]-1-phenethyl urea (Compound 3-3)

[α] D20:−52.1° (c=0.52, chloroform)

IR (Film, cm$^{-1}$): 3384, 3027, 2951, 1631, 1525, 1455, 751 and 702

1-[(1S)-1-Benzyl-2-hydroxyethyl]-3-[2-(t-butoxycarboxamido)ethyl]-3-isopentyl urea (Compound 3-4)

[α] D20:−26.8° (c=0.95, chloroform)

IR (Film, cm$^{-1}$): 3328, 2956, 1687, 1627, 1524, 1367, 1283, 1251, 1171, 756 and 701

Example 4:
1-[(1S)-1-(Benzyloxycarbonyl)-2-(4-biphenylyl) ethyl]-3-[2-(dimethylamino)ethyl]-3-isopentyl urea (Compound 4-1)

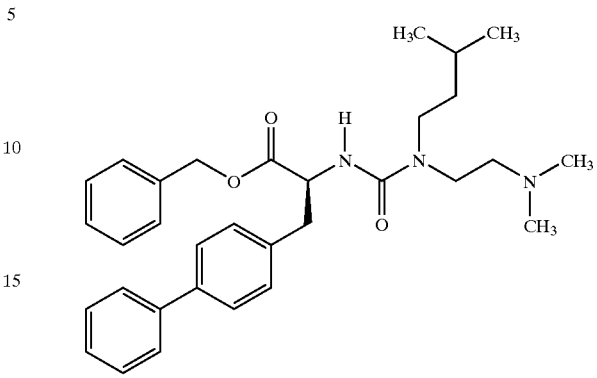

To a suspension of 4-biphenylyl-L-alanine benzyl ester hydrochloride (270 mg) in anhydrous tetrahydrofuran (2 ml), there were added imidazole (50 mg) and 1,1'-carbonyl diimidazole (155 mg) in the nitrogen gas atmosphere and the resulting mixture was stirred at room temperature for 10 minutes. Then a solution of N-isopentyl-2-(dimethylamino) ethylamine (Reference Compound 2-2, 589 mg) in anhydrous tetrahydrofuran (3 ml) was added to the mixture, followed by the reflux with heating for 1.5 hour. Chloroform was added to this reaction liquid under ice cooling, the reaction liquid was washed with saturated sodium hydrogen carbonate aqueous solution and then with saturated sodium chloride aqueous solution, dried over anhydrous sodium sulfate and then concentrated under reduced pressure. The resulting oily product was purified through the silica gel column chromatography to give the title compound (Compound 4-1, 402 mg).

(Compound 4-1)

[α] D20:−8.7° (c=0.49, chloroform)

IR (Film, cm$^{-1}$): 2953, 1741, 1650, 1519, 1487, 1466, 1252, 758 and 698

The procedures similar to those used in Example 4 were repeated to give the following compound.

1-[(1S)-1-(Benzyloxycarbonyl)-2-(4-biphenylyl) ethyl]-3-[2-(t-butoxycarboxamido)ethyl]-3-isopentyl urea (Compound 4-2)

[α] D20:−18.8° (c=0.97, chloroform)

IR (Film, cm$^{-1}$): 3324, 2957, 1740, 1684, 1637, 1518, 1454, 1172 and 756

Example 5:
1-[(1S)-1-[(4-Biphenylyl)methyl]-2-hydroxyethyl]-3-[2-(dimethylamino)ethyl]-3-isopentyl Urea (Compound 5-1)

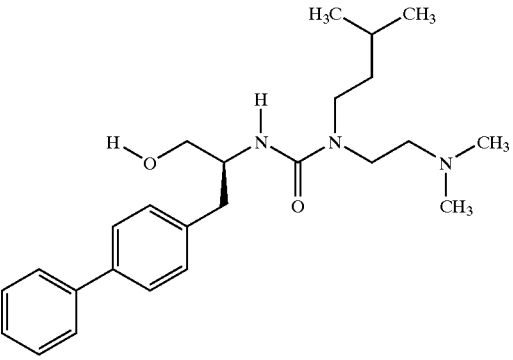

Lithium bromide (179 mg) and sodium boron hydride (52 mg) were suspended in anhydrous ethanol (1 ml) in the nitrogen gas atmosphere and the resulting suspension was stirred at room temperature for one hour. To the suspension, there was dropwise added a solution of 1-[(1S)-1-(benzyloxycarbonyl)-2-(4-biphenylyl) ethyl]-3-[2-(dimethylamino)ethyl]-3-isopentyl urea (Compound 4-1, 310 mg) in anhydrous ethanol (5.8 ml) with ice cooling. The resulting mixture was stirred at room temperature for 24 hours. Saturated ammonium chloride aqueous solution was added to the reaction liquid with ice cooling and then the resulting mixture was extracted with ether. The resulting organic phase was washed with saturated sodium chloride aqueous solution, dried over anhydrous magnesium sulfate and then concentrated under reduced pressure. The resulting oily product was purified through the silica gel column chromatography to give the title compound (Compound 5-1, 138 mg).
(Compound 5-1)
[α] D20:−37.9° (c=0.20, chloroform)
IR (Film, cm$^{-1}$): 3358, 2953, 1628, 1521, 1487, 1467, 762 and 698

The procedures similar to those used in Example 5 were repeated to give the following compound.
1-[(1S)-1-[(4-Biphenylyl)methyl]-2-hydroxyethyl]-3-[2-(t-butoxycarboxamido)ethyl]-3-isopentyl urea (Compound 5-2)
[α] D20:−35.1° (c=0.48, chloroform)
IR (Film, cm$^{-1}$): 3329, 2956, 1687, 1627, 1520, 1366, 1250, 1170 and 761

Example 6:

1-[2-(Acetylthio)ethyl]-1-(2-cyclohexyl ethyl)-3-[2-(dimethylamino)ethyl] Urea (Compound 6-1)

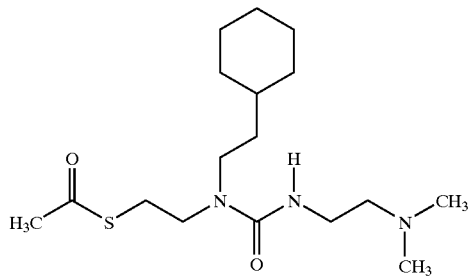

1-(2-Cyclohexyl ethyl)-3-[2-(dimethylamino)ethyl]-1-(2-hydroxyethyl)-urea (Compound 1-1, 0.57 g) and triphenyl phosphine (1.04 g) were dissolved in anhydrous tetrahydrofuran (10 ml) in the nitrogen gas atmosphere and the resulting solution was stirred under cooling with sodium chloride-ice for 30 minutes. Diisopropyl azodicarboxylate (0.78 ml) and a solution of thioacetic acid (0.30 g) in anhydrous tetrahydrofuran (1 ml) were dropwise added to the solution while maintaining the temperature of the solution to a level of not higher than 5° C. After stirring the solution for one hour, saturated sodium hydrogen carbonate aqueous solution was added to the reaction solution and the resulting mixture was extracted with ethyl acetate. The resulting organic phase was washed with saturated sodium chloride aqueous solution, dried over anhydrous sodium sulfate and then concentrated under reduced pressure. The resulting oily product was purified through the silica gel column chromatography to give the title compound (Compound 6-1, 0.43 g).
(Compound 6-1)
IR (Film, cm$^{-1}$): 3367, 2924, 2852, 2771, 1692, 1633, 1533, 1449, 1406, 1356, 1294, 1187 and 1137

The procedures similar to those used in Example 6 were repeated to give the following compounds.

1-[2-(Acetylthio)ethyl]-1-(2-cyclohexyl ethyl)-3-[3-(dimethylamino)propyl]-urea (Compound 6-2)

IR (Film, cm$^{-1}$): 3352, 2923, 2851, 2816, 1692, 1632, 1534, 1448, 1405, 1356, 1294, 1217 and 1135

1-[2-(Acetylthio)ethyl]-3-[(1S)-1-benzyl-2-(dimethylamino)ethyl]-1-phenethyl urea (Compound 6-3)

[α] D20:−26.2° (c=1.0, methanol)

IR (Film, cm$^{-1}$): 3392, 2940, 1682, 1644, 1531, 1497, 1454, 1138, 750 and 701

1-[2-(Acetylthio)ethyl]-1-(2-cyclohexyl ethyl)-3-[3-[(N-methyl)-phenylamino]propyl] urea (Compound 6-4)

IR (Film, cm$^{-1}$): 3348, 2922, 2850, 1690, 1630, 1599, 1506, 1291, 1217 and 1135

1-[2-(Acetylthio)ethyl]-1-isopentyl-3-[2-(dimethylamino) ethyl]urea (Compound 6-5)

IR (Film, cm$^{-1}$): 3367, 2954, 2361, 1690, 1632, 1532, 1360, 1296, 1235, 1136, 950 and 766

1-[2-(Acetylthio)ethyl]-1-(2-cyclohexyl ethyl)-3-[2,2-dimethyl-3-(dimethylamino)propyl] urea (Compound 6-6)

IR (Film, cm$^{-1}$): 3305, 2923, 2852, 2776, 1693, 1641, 1524, 1450, 1355, 1293, 1218, 1136, 1040, 950, 844 and 753

1-[(1S)-2-(Acetylthio)-1-benzylethyl]-3-[2-(dimethylamino)ethyl]-3-phenethyl urea (Compound 6-7)

[α] D20:+15.9° (c=1.0, chloroform)

IR (Film, cm$^{-1}$): 3350, 2943, 1691, 1648, 1602, 1253, 1136 and 701

1-[(1S)-2-(Acetylthio)-1-benzylethyl]-3-[2-(dimethylamino)ethyl]-3-isopentyl urea (Compound 6-8)

[α] D20:+22.4° (c=0.44, chloroform)

IR (Film, cm$^{-1}$): 3351, 2953, 1694, 1651, 1524 and 701

1-[(1S)-2-(Acetylthio)-1-benzylethyl]-3-[(1S)-1-benzyl-2-(dimethylamino)-ethyl]-3-phenethyl urea (Compound 6-9)

[α] D20:−32.0° (c=0.55, chloroform)

IR (Film, cm$^{-1}$): 3416, 2937, 1690, 1644, 1496, 749 and 700

1-[(1S)-2-(Acetylthio)-1-benzylethyl]-3-[2-(t-butoxycarboxamido)-ethyl]-3-isopentyl urea (Compound 6-10)

[α] D20:+7.0° (c=0.52, chloroform)

IR (Film, cm$^{-1}$): 3316, 2957, 1690, 1632, 1528, 1252 and 701

1-[(1S)-2-(Acetylthio)-1-[(4-biphenylyl) methyl]ethyl]-3-[2-(dimethylamino)-ethyl]-3-isopentyl urea (Compound 6-11)

[α] D20:+15.9° (c=0.47, chloroform)

IR (Film, cm$^{-1}$): 2953, 1693, 1651, 1519, 1250, 1136 and 762

1-[(1S)-2-(Acetylthio)-1-[(4-biphenylyl)methyl]ethyl]-3-[2-(t-butoxycarboxamido)ethyl]-3-isopentyl urea (Compound 6-12)

[α] D20:+6.0° (c=0.49, chloroform)

IR (Film, cm$^{-1}$): 3316, 2956, 1686, 1632, 1520, 1366 and 761

Example 7:

Bis [(2S)-2-[3-[2-(t-butoxycarboxamido)ethyl]-3-isopentyl ureido]-3-phenylpropane] Disulfide (Compound 7-1)

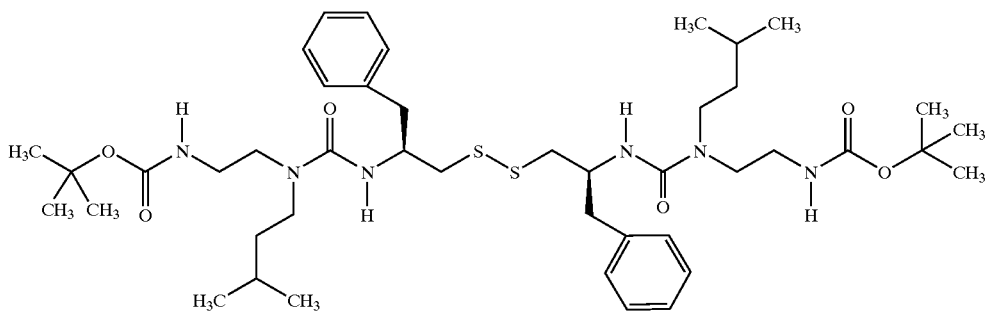

To a solution of 1-[(1S)-2-(acetylthio)-1-benzylethyl]-3-[2-(t-butoxycarboxamido)ethyl]-3-isopentyl urea (Compound 6-10, 169 mg) in tetrahydrofuran (4 ml), there were added 28% aqueous ammonia (10 ml) and a small amount of iodine crystal and the resulting mixture was stirred at room temperature overnight. Water was added to the reaction solution and the mixture was extracted with ether. The resulting organic phase was washed with a 10% sodium thiosulfate aqueous solution and saturated sodium chloride aqueous solution, dried over anhydrous sodium sulfate and then concentrated under reduced pressure. The resulting oily product was purified through the silica gel column chromatography to thus give the title compound (Compound 7-1, 70 mg).

(Compound 7-1)

[α] D20:+30.7° (c=0.14, chloroform)

IR (Film, cm$^{-1}$): 3316, 2956, 1684, 1629, 1532, 1454, 1366, 1171 and 752

The procedures similar to those used in Example 7 were repeated to thus give the following compound.

Bis[(2S)-2-[3-[2-(t-butoxycarboxamido)ethyl]-3-isopentyl ureido]-3-(4-biphenylyl)propane] disulfide (Compound 7-2)

[α] D20:+12.8° (c=0.26, chloroform)

IR (Film, cm$^{-1}$): 3321, 2957, 1684, 1630, 1520, 1366, 1250, 1170 and 760

Example 8:

Bis[(2S)-2-[3-(2-aminoethyl)-3-isopentyl ureido]-3-phenylpropane] Disulfide di-hydrochloride (Compound 8-1)

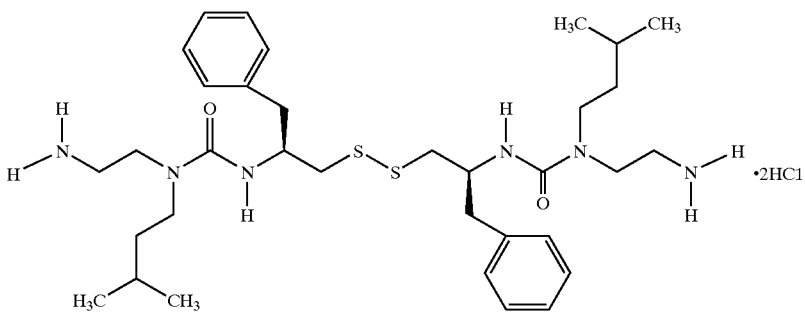

To a solution of bis[(2S)-2-[3-[2-(t-butoxycarboxamido)ethyl]-3-isopentyl ureido]-3-phenylpropane] disulfide (Compound 7-1, 53 mg) in chloroform (0.6 ml), there was added a 4.6N solution of hydrogen chloride in ethyl acetate (0.3 ml) in the nitrogen gas atmosphere. After stirring the resulting mixture at room temperature for 24 hours, it was concentrated under reduced pressure. Isopropyl ether was added to the resulting residue and the resulting precipitates were filtered to thus give the title compound (Compound 8-1, 21 mg) in the form of crystals.

(Compound 8-1)

mp: 100° C. (decomposed)

IR (KBr, cm$^{-1}$): 3326, 2956, 1619, 1535, 748 and 701

The procedures similar to those used in Example 8 were repeated to give the following compound.

Bis[(2S)-2-[3-(2-aminoethyl)-3-isopentyl ureido]-3-(4-biphenylyl)propane]- disulfide di-hydrochloride (Compound 8-2)
mp: 132.0~136.0° C.
IR (KBr, cm$^{-1}$): 2956, 1617, 1531, 762 and 699

[EXAMPLES OF PHARMACEUTICAL PREPARATIONS]

Examples of general formulations of orally administered drugs and injections containing the compounds of the present invention will be given below.

1) Tablets: Formulation 1 (per 100 mg)

| Compound of the Present Invention | 1 mg |
|---|---|
| Lactose | 66.4 mg |
| Corn Starch | 20 mg |
| Calcium Carboxymethylcellulose | 6 mg |
| Hydroxypropylcellulose | 4 mg |
| Magnesium Stearate | 0.6 mg |

Each tablet having the foregoing formulation was coated with 2 mg of a coating agent (for instance, a currently used coating agent such as hydroxypropylmethylcellulose, macrogol or a silicone resin) to thus give a desired coated tablet (the tablets having the following formulations were likewise be prepared by the same method). In addition, desired tablets can be prepared by appropriately and variously changing the amounts of the compound according to the present invention and various additives.

2) Capsules: Formulation 1 (per 150 mg)

| Compound of the Present Invention | 5 mg |
|---|---|
| Lactose | 145 mg |

Desired capsules can be prepared by appropriately and variously changing the mixing ratio of the compound of the present invention to lactose.

3) Injections: Formulation 1 (per 10 ml)

| Compound of the Present Invention | 10 to 100 mg |
|---|---|
| Sodium Chloride | 90 mg |
| Sodium Hydroxide (or Hydrochloric Acid) | Sufficient Quantity |
| Sterilized and Purified Water | Sufficient Quantity |

Desired injections can be prepared by appropriately and variously changing the mixing ratio of the compound of the present invention to the additives.

[Pharmacological Tests]

Each candidate compound was inspected for the effect of inhibiting TNF-α production induced by the stimulation with lipopolysaccharide (LPS), by an in vitro test according to the method proposed by McGeehan et al. (Nature, 1994, 370:558–561).

The test (assay) was carried out by determining the amount of TNF-α produced by the human monocyte strain THP-1 cells induced by the stimulation with LPS.

The culture medium used in this test was RPMI 1640 culture medium supplemented wiTNFetal calf serum (10%), L-glutamine (2 mM), 2-mercaptoethanol (50 μM), penicillin (50 units/ml) and streptomycin (50 μg/ml).

Regarding the cells, the human monocyte strain THP-1 cells cultivated in the foregoing culture medium were centrifuged at 100 xg for 5 minutes to remove the supernatant and then again suspended in a fresh culture medium prior to the practical use. The LPS used herein was derived from S. Typhimurium and this was dissolved in purified water and then this was dissolved in purified water and then diluted with the culture medium prior to use. Each compound to be tested (candidate compound) was dissolved in dimethyl sulfoxide (DMSO) and diluted with the culture medium prior to the practical use.

The cells ($10^6$ cells/ml) prepared according to the foregoing method were admixed with the LPS (2 μg/ml) and a compound to be tested ($10^{-5}$M), the cells were incubated at 37° C. for two hours and then centrifuged at 1000 xg for 5 minutes. The resulting supernatant of the culture medium was inspected for the level of TNF-α using the human TNF-α-specific ELISA kit. In this connection, it was confirmed that the supernatant obtained by cultivating the cells in the culture medium free of any LPS (control) never included any TNF-α.

The rate of the TNF-α production inhibitory effect observed for each candidate compound was determined according to the following equation:

Rate of Inhibition (%)=100×(A−B)/A

Wherein A is the level of TNF-α detected in the supernatant obtained from the culture medium free of any candidate compound and B is the level of TNF-α detected in the supernatant obtained from the culture medium containing a candidate compound.

(Results)

A few test results, by way of example, or the inhibitory rate (%) of TNF-α production observed at the concentration of $10^{-5}$M are shown in the following Table 1.

TABLE 1

| Candidate Compound | Rate of Inhibition (%) |
|---|---|
| Compound 6-3 | 83 |
| Compound 6-8 | 60 |
| Compound 6-11 | 76 |
| Compound 8-1 | 81 |
| Compound 8-2 | 66 |

As will be seen from the results listed in Table 1, it was recognized that the compounds of the present invention show the TNF-α production-inhibitory effect at a low concentration.

As has been discussed above in detail, the compound of the present invention has an excellent TNF-α production inhibitory effect and it is clear that the compound has wide variety of applications as pharmaceutical agents such as therapeutic agents for diseases, in which TNF-α is involved, for instance, autoimmune diseases such as chronic articular rheumatism, Crohn's disease and systemic erythematodes, dyscrasia, acute infectious diseases, allergy, fever, anemia and diabetes.

What is claimed is:

1. An N-substituted-N substituted urea derivative represented by the following general formula I and a pharmaceutically acceptable salt thereof:

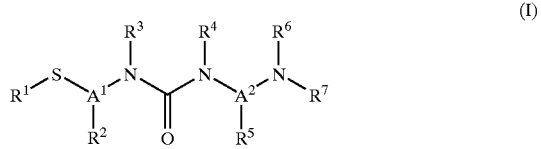

(I)

wherein $R^1$ represents a hydrogen atom, a lower alkyl group, an aryl group selected from the group consisting of phenyl substituted with a cycloalkyl group, and phenyl substituted with a phenyl group, or $R^1$ represents a group represented by the following general formula II:

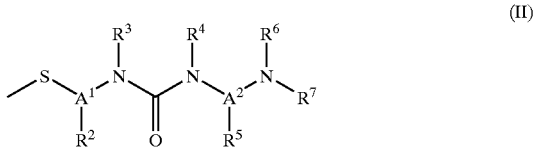

wherein $R^2$ represents a hydrogen atom, a lower alkyl group, a cycloalkyl group, an aryl group, a carboxyl group or an ester group, or $R^2$ may form a ring together with $R^1$; $R^3$ and $R^4$ may be the same or different and each represents a hydrogen atom, a lower alkyl group, a cycloalkylalkyl group, an arylalkyl group, a cycloalkyl group or an aryl group; $R^5$ represents a hydrogen atom, a lower alkyl group, a hydroxyl group, a lower alkoxy group or an aryl group; $R^6$ and $R^7$ may be the same or different and each represents a hydrogen atom, a lower alkyl group, a cycloalkylalkyl group, a cycloalkyl group or an aryl group; $A^1$ and $A^2$ may be the same or different and each represents a lower alkylene group, provided that if both $R^6$ and $R^7$ are methyl groups, $R^1$, $R^3$ and $R^4$ do not simultaneously represent hydrogen atom, or if $R^3$ is an isopropyl group and both $R^6$ and $R^7$ are methyl groups, $R^1$ does not represent an aryl group.

2. The urea derivative and pharmaceutically acceptable salt thereof as set forth in claim 1, wherein in the general formula I, $R^1$ is a hydrogen atom, a lower alkyl group or a group represented by Formula II, $R^2$ is a hydrogen atom or an aryl group, $R^3$ and $R^4$ may be the same or different and each represents a hydrogen atom, a lower alkyl group, a cycloalkylalkyl group or an arylalkyl group, $R^5$ is a hydrogen atom, a lower alkyl group, a hydroxyl group or an aryl group, $R^6$ and $R^7$ may be the same or different and each represents a hydrogen atom, a lower alkyl group or an aryl group, and $A^1$ and $A^2$ may be the same or different and each represents an alkylene group having 2 to 4 carbon atoms.

3. The urea derivative and pharmaceutically acceptable salt thereof as set forth in claim 2, wherein in the general formula I, $R^6$ represents a hydrogen atom or a lower alkyl group, $R^7$ represents a hydrogen atom, a lower alkyl group or an aryl group, $A^1$ is an alkylene group having 2 or 3 carbon atoms and $A^2$ is an alkylene group having 2 to 4 carbon atoms.

4. The urea derivative and pharmaceutically acceptable salt thereof as set forth in claim 1, wherein in the general formula I, $R^3$ is a hydrogen atom, a cycloalkylalkyl group or an arylalkyl group, $R^4$ is a hydrogen atom, a lower alkyl group or an arylalkyl group and either $R^3$ or $R^4$ represents a hydrogen atom.

5. The urea derivative and pharmaceutically acceptable salt thereof as set forth in claim 1, wherein in the general formula I, $R^5$ is a hydrogen atom, a lower alkyl group or an aryl group.

6. The urea derivative and pharmaceutically acceptable salt thereof as set forth in claim 1, wherein in the general formula I, if $R^1$ is a hydrogen atom, it may be protected with a lower alkylcarbonyl group at the position of $R^1$.

7. A compound selected from the group consisting of 1-[2-(acetylthio)ethyl]-3-[(1S)-1-benzyl-2-(dimethylamino) ethyl]-1-phenethyl urea, 1-[(1S)-2-(acetylthio)-1-benzylethyl]-3-[2-(dimethylamino) ethyl]-3-isopentyl urea, 1-[(1S)-2-(acetylthio)-1-[(4-biphenylyl)methyl]ethyl]-3-[2-(dimethylamino)-ethyl]-3-isopentyl urea, bis[(2S)-2-[3-(2-aminoethyl)-3-isopentyl ureido]-3-phenylpropane] disulfide and bis[(2S)-2-[3-(2-aminoethyl)-3-isopentyl-ureido]-3-(4-biphenylyl)propane] disulfide and a pharmaceutically acceptable salt thereof.

8. A pharmaceutical composition containing an N-substituted-N'-substituted urea derivative or a pharmaceutically acceptable salt thereof as set forth in claim 1.

9. A pharmaceutical composition containing an N-substituted-N'-substituted urea derivative or a pharmaceutically acceptable salt thereof as set forth in claim 2.

10. A pharmaceutical composition containing an N-substituted-N'-substituted urea derivative or a pharmaceutically acceptable salt thereof as set forth in claim 3.

11. A pharmaceutical composition containing a compound or a pharmaceutically acceptable salt thereof as set forth in claim 7.

12. A TNF-α production inhibitory agent comprising an N-substituted-N'-substituted urea derivative or a pharmaceutically acceptable salt thereof as set forth in claim 1.

13. A TNF-α production inhibitory agent containing an N-substituted-N'-substituted urea derivative or a pharmaceutically acceptable salt thereof as set forth in claim 2.

14. A TNF-α production inhibitory agent containing an N-substituted-N'-substituted urea derivative or a pharmaceutically acceptable salt thereof as set forth in claim 3.

15. A TNF-α production inhibitory agent containing a compound or a pharmaceutically acceptable salt thereof as set forth in claim 7.

16. A therapeutic agent for autoimmune diseases comprising an N-substituted-N'-substituted urea derivative or a pharmaceutically acceptable salt thereof as set forth in claim 1.

17. A therapeutic agent for autoimmune diseases containing an N-substituted-N'-substituted urea derivative or a pharmaceutically acceptable salt thereof as set forth in claim 2.

18. A therapeutic agent for autoimmune diseases containing an N-substituted-N'-substituted urea derivative or a pharmaceutically acceptable salt thereof as set forth in claim 3.

19. A therapeutic agent for autoimmune diseases containing a compound or a pharmaceutically acceptable salt thereof as set forth in claim 7.

20. The urea derivative and pharmaceutically acceptable salt thereof as set forth in claim 1 wherein $R^1$ is selected from the group consisting of a hydrogen atom, a lower alkyl group and the group represented by the formula II.

* * * * *